United States Patent [19]

Cussac et al.

[11] Patent Number: 5,277,069
[45] Date of Patent: Jan. 11, 1994

[54] DEVICE FOR TESTING TEST PIECES BENDING IN AN AMBIENT CRYOGENIC ENVIRONMENT

[75] Inventors: Michel Cussac, La Teste; Jean F. Fuchs, St. Helene, both of France

[73] Assignee: Aerospatiale Societe Nationale Industrielle, Paris, France

[21] Appl. No.: 855,313

[22] Filed: Mar. 23, 1992

[30] Foreign Application Priority Data

Apr. 22, 1991 [FR] France .................. 91 04921

[51] Int. Cl.$^5$ .............................................. G01N 3/20
[52] U.S. Cl. ...................................................... 73/853
[58] Field of Search ................. 73/849, 850, 851, 852, 73/853, 854

[56] References Cited

U.S. PATENT DOCUMENTS

| 2,504,985 | 4/1950 | Kallas et al. ................. 73/15.4 |
| 3,158,021 | 11/1964 | Walters et al. ................. 73/100 |
| 4,976,152 | 12/1990 | McKinley et al. ................. 73/852 |
| 5,187,987 | 2/1993 | Anderson et al. ................. 73/852 |

FOREIGN PATENT DOCUMENTS

| 2533373 | 1/1977 | Fed. Rep. of Germany . |
| 2638006 | 3/1978 | Fed. Rep. of Germany . |
| 59265047 | 6/1986 | Japan ................. G01N 3/32 |
| 62-148445 | 12/1988 | Japan ................. G01N 3/20 |

OTHER PUBLICATIONS

2422 Industrial Laboratory vol. 43 No. 9 (Sep. 1977) "Micromachine For Low-Frequency Fatigue Testing of Materials by Pure Bending" By: Maksimovich et al. pp. 1309-1310.

Transactions of the ASME Oct. 1974. "Predicting the Fracture Initiation Transition Temperature in High Toughness, Low Transition Temperature Line Pipe With the COD Test" By: Podlasek et al. pp. 330-334.

*Primary Examiner*—Jerry W. Myracle
*Attorney, Agent, or Firm*—Hayes, Soloway, Hennessey & Hage

[57] ABSTRACT

A device for low temperature bend-testing of a test piece is disclosed. The device of the present invention comprises fixed and movable units. The fixed unit includes a base which includes at least one substantially vertical stanchion. A tank for holding a volume of low temperature liquid, such as liquid nitrogen, is secured to the base. The movable unit includes a support and a pin. The support structure includes an arch portion and at least one projection. The test piece under test is supported by supports included in the arch portion. The pin is slidably mounted in the structure so as to be displaceable in a direction perpendicular to the test piece when supported by the supports. The device also includes means making the fixed and movable units operable together to permit the test piece to be bend-tested in the tank.

9 Claims, 3 Drawing Sheets

DEVICE FOR TESTING TEST PIECES BENDING IN AN AMBIENT CRYOGENIC ENVIRONMENT

FIELD OF THE INVENTION

The invention concerns a device for testing test pieces bending in an ambient cryogenic environment.

BACKGROUND OF THE INVENTION

There already exist a certain number of devices for the bending testing of test pieces and which mainly include a test piece support structure secured to a base and provided with two rollers on which the test piece extremities are laid, and a pin sliding with respect to one portion of the base perpendicular to the test piece on which it is pressed halfway between the supports. It is then possible to conduct conventional tests for measuring the force on rupture or measure bending according to the force applied to the pin.

Some of these devices are completed by a chamber surrounding the test piece and the pin, this making it possible to test in special conditions the temperature, atmosphere, etc., but tests conducted at extremely low temperatures require that the test piece be immersed into a cryogenic liquid, such as liquid nitrogen, which poses new problems in this field as it becomes difficult or impossible to measure the bending of the test piece by conventional methods with stress gauges or with direct reading, the use of the cryogenic fluid rendering handlings of the device as being scarcely practical. If, for example, it is desired to carry out several successive tests, it is impractical to on each occasion empty the liquid contained in the chamber so as to fill it again as soon as the test piece is replaced.

SUMMARY OF THE INVENTION

The object of the invention is thus to provide a device for testing bending test pieces able to function effectively in cryogenic conditions and for conducting a large number of tests without encountering any difficulties concerning handling and without the liquid being wasted. This device includes the following: a structure fitted with extreme supports for one test piece; a pin sliding with respect to a fixed base and perpendicular to the test piece laid on the supports, the pin comprising one extremity for pressing the test piece between the supports. This device is characterized in that the base includes a tank intended to be filled with liquid at a low temperature with at least one stanchion lifted up; the support structure of the test piece is mobile with respect to the base and includes one arch and at least one projection, the projections extending above the stanchions; and the pin includes one shoulder extending below the arch, the structure being able to be immersed into and removed from the tank. Thus, the invention concerns a test piece support structure, namely a mobile piece able to be laid either on the base during the tests, or on the pin between tests when said pin is lifted up with cryogenic liquid.

It is advantageous that the arch comprises a bore inside which the pin is able to slide.

A suitable device for measuring the bending of the test piece consists of a rod traversing the pin and extending as far as the test piece, and at least one reference scale secured to the base.

In one particular embodiment provided for bending tests on four points and in which the pressing extremity of the pin consists of one lever linked to the pin by a joint and fitted with two pressing knives on the test piece on both sides of the joint, the measuring device is modified so that the rod then traverses the joint and the axis of the latter.

It is often preferable to fit the test piece support structure with a device for blocking the test piece on the supports so as to eliminate the risks of the test piece moving or floating as soon as it is immersed in the liquid.

BRIEF DESCRIPTION OF THE DRAWINGS

The invention is now to be described with the aid of the following accompanying figures and an illustrative and non-restrictive example of one embodiment of the invention.

DETAILED DESCRIPTION OF THE PREFERRED EMBODIMENTS

Figure 1:
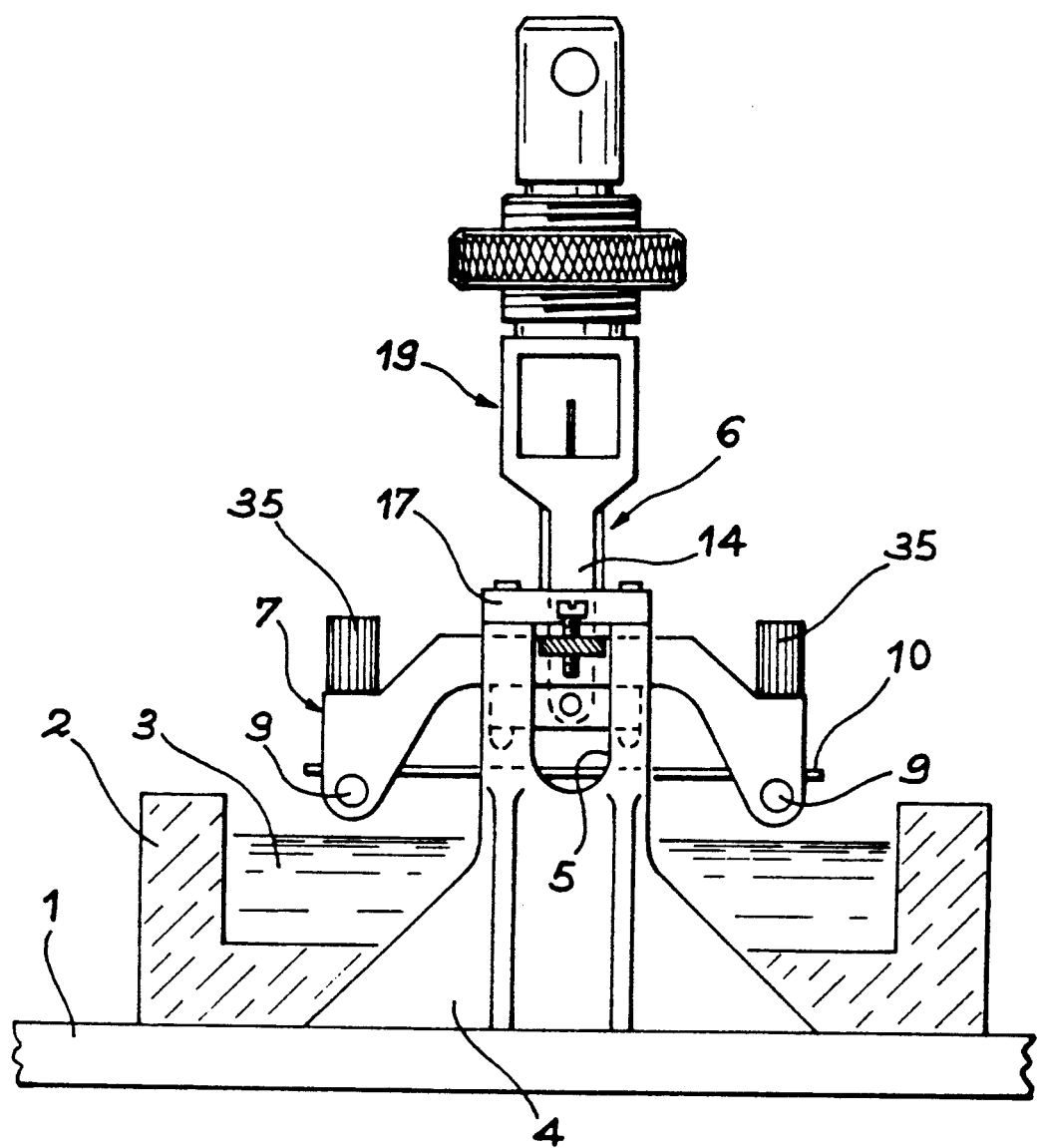
FIG. 1 shows a front full view of the device.

The device firstly comprises (FIG. 1) a flat base 1 on which a tank 2 is erected, said tank intended to be filled with cryogenic liquid 3, such as liquid nitrogen, and stanchions 4 on the longitudinal sides of the tank 2. The stanchions 4, only one being shown on FIG. 1, are identical and each comprise a vertical groove 5 which notches them from the top.

Figure 3:
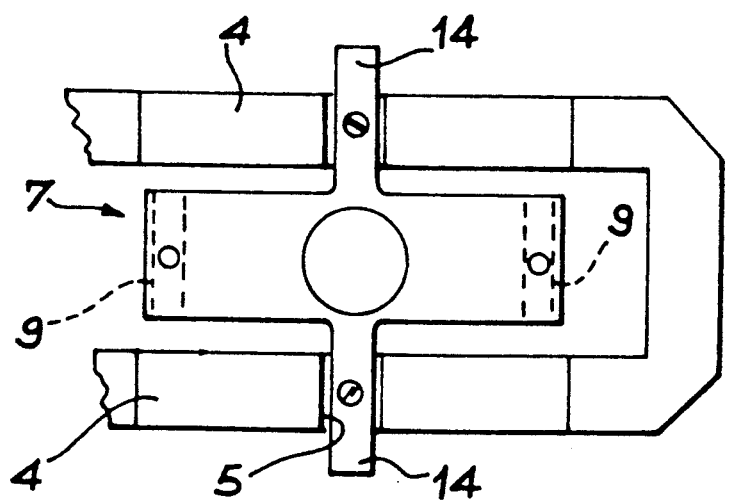
FIG. 3 shows a top view of the pin and the test piece bearing structure.

These stationary portions of the device cooperate with a mobile unit mainly consisting of two portions: a pin 6 and a support structure 7. The support structure 7, clearly visible on FIG. 2, mainly comprises an arch 8 whose extremities bent back towards the bottom each comprise a roller 9 on which the plate or blade-shaped extremities of a test piece 10 are laid and which are to be bent. At its middle, the arch 8 comprises a bore 11 having one widened portion 12 limited by a shoulder bearing 13. Finally, FIG. 3 shows that the support structure 7 comprises two horizontal projections 14 and forming an extension perpendicular to the arch 8, these projections having the shape of wings and penetrating into a respective groove 5. The projections 14 are situated at the top of the arch 8 so that they do not touch the bottom of the grooves 5 when the test piece 10 remains immersed in the cryogenic liquid 3. The main role of the projections 14 is to keep the support structure 7 and thus the test piece 10 in a constant longitudinal position with respect to the tank 2 and the pin 6, while enabling the support structure 7 to slide vertically.

Figure 2:
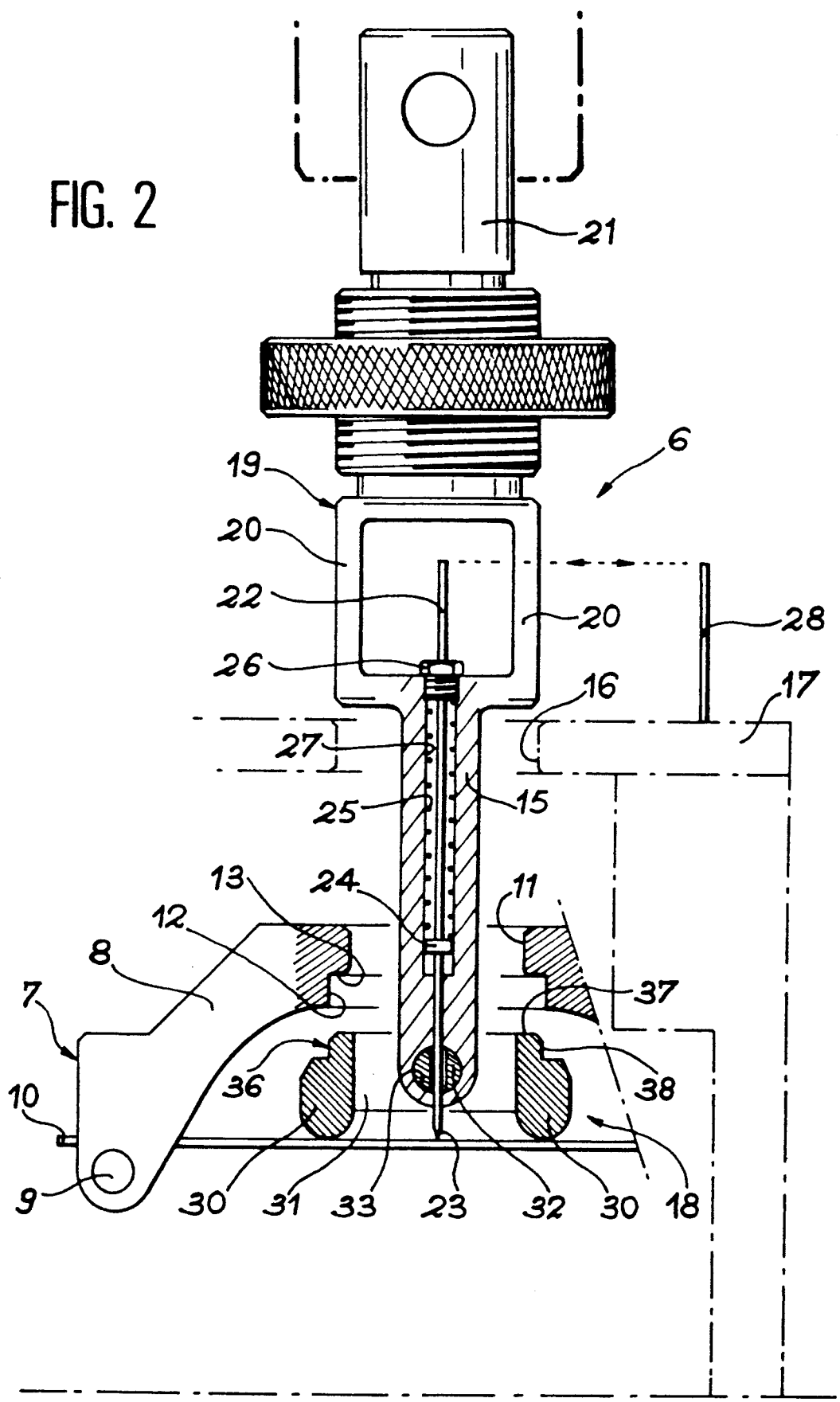
FIG. 2 shows in more detail the pin and the structure bearing the test piece.

The pin 6 is mainly illustrated on FIG. 2. It comprises a rod 15 extending through the bore 11 and one upper bore 16 fitted on a cover 17 which connects the top of the two stanchions 4, one lower pressing extremity intended to be pressed on the test piece 10, thus embodying the bending test, one widened portion 19 composed of two guiding walls 20 in the upper bore 16 and one joining piece 21 for fixing to a pressing machine (not shown in detail) secured to the base 1. One particular element of the pin 6 is a sensor rod 22 extending into a bore 27 embodied through the rod 15 along its axis.

The sensor rod 22 is ended by a needle punch 23 intended to touch the test piece 10 and thus subsequently go past the extremity of the pressing extremity 18. It also includes one small collar 24 on which a spring 25 wound around the upper portion of the sensor rod 22 is compressed and exerts a pressure keeping the needle punch against the test piece 10. A pierced nut 26 closes the top of the pressing 27 and keeps the spring 25 compressed inside the bore 27 whilst allowing the top of the sensor rod 22 to go past; a marker 28, such as a graduated strip, located on the cover makes it possible to monitor and measure the movements of the top of the sensor rod 22.

The pressing extremity 18 shown on FIGS. 1 and 2 is a built-on piece intended to subject the test piece 10 to bending at four points. It is composed of two knives 30 offering linear contact over the width of the test piece 10 in the direction of the rollers 9, and a lever 31 bringing the knives 30 together and which rotates around a spindle 32 driven into one recess 33 of the rod 15. This linkage enables the pressing extremity 18 to tilt so as to still rest on the test piece 10 by virtue of the two knives 30 situated on both sides of the spindle 32. However, it is essential that the spindle 32 be hollowed, as with the rod 15, so as to allow for passage to the sensor rod 22. The test piece 10 is bent in conditions depending on the locations of the knives 30 and the rollers 9. If these locations are symmetrical, pure bending stresses are produced between the knives 30.

Figure 4:
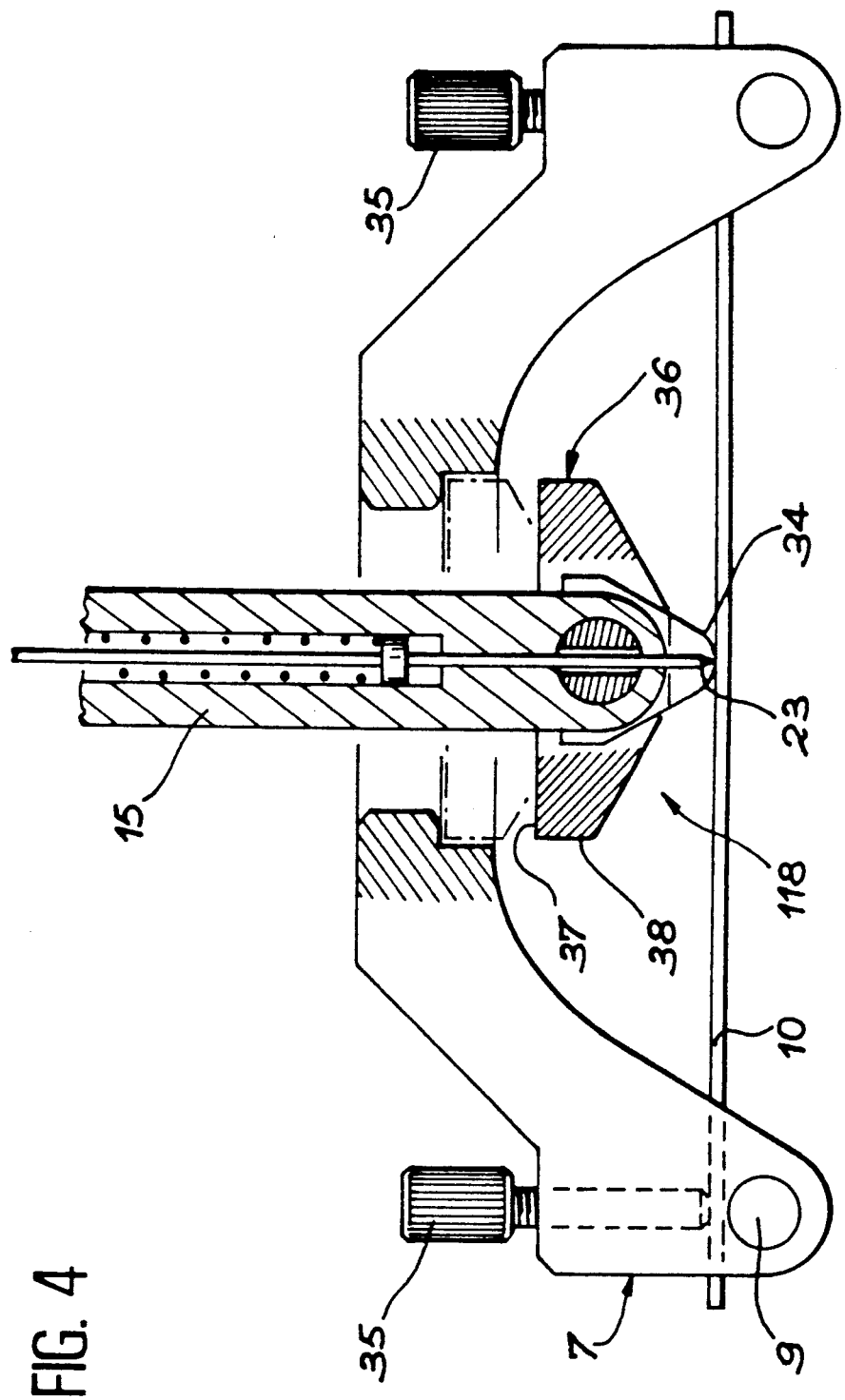
FIG. 4 shows another stanchion.

If, however, one is merely satisfied with a bending on three points, that is on the rollers 9 and one intermediate pressing point, the pressing extremity 18 is replaced by one pressing extremity 118 comprising a single knife 34 in the prolongation of the rod 15. This pressing extremity 118 (shown on FIG. 4) is rigidly secured to the rod 15.

Both the extremity 18 and the extremity 118 comprise an upper shoulder 36, whose upper face 37 is intended to lean on the shoulder bearing 13, as well as a cylindrical surface 38 provided so as to slide into the extension 12.

Finally, there are two screws 35 engaged into the arch 8 above the rollers 9. These are fixing screws which press the extremities of the test piece 10 onto the rollers 9 and thus prevent it from being removed from the support structure 7.

When a test cycle starts, the pin 6 is lifted up, as well as the support structure 7 once the shoulder bearing 13 rests on the upper face 37 of the pressing extremity 18 or 118. The liquid nitrogen present is then subsequently renewed or added to. A new test piece 10 is slid onto the rollers 9.

Then the pin 6 is gradually lowered again with the aid of the pressing machine from the joining piece 21. The test piece 10 dips into the liquid nitrogen and then the projections 14 touch the bottom of the grooves 5, after which the support structure 7 is no longer resting on the pin 6 and remains immobile. It is then easily possible to release the screws 35 so as to free the extremities of the test piece 10. If the test piece 10 has simply been laid on the rollers 9 when immersed in the liquid nitrogen 3, it would have been able to be moved by the boiling and slight waves of the liquid. The lowering of the pin 6 nevertheless continues until the knives 30 or 34 touch the upper face of the test piece 10. This then occurs when calibrating the device and corresponding to a nil deflection of the test piece 10 and to a particular force applied, also nil. Any additional movement of the pin 6 towards the bottom provokes bending of the test piece 10. The force applied is directly measured by the machine and deflection by the device constituted by the marker 28 and the sensor rod 22. The guiding walls 20 then slide into the upper bore 16, thus guaranteeing centering of the pin 6 and the test piece 10 in combination with the projections 14 and grooves 5 since the latter and the upper bore 16 form part of the same unit. When the test piece 10 needs to be replaced, the pin 6 is lifted up until the entire support structure is lifted up and comes out of the liquid nitrogen 3. A new test piece 10 is then installed instead of the old one and the test is restarted.

The test pieces 10 may in particular be test pieces made of composite materials.

What is claimed is:

1. A device for low temperature bend-testing of an elongated test piece between its ends, and comprising:
   a. a support structure comprising an arch portion and at least one projection, said arch portion comprising: (i) lower supports for supporting the ends of said test piece, and (ii) a middle portion;
   b. a base;
   c. a tank secured to said base for containing a volume of a low temperature liquid;
   d. a pin slidably mounted in said support structure and displaceable in a direction perpendicular to a test piece supported by said supports, said pin including a shoulder portion which extends under said middle portion of said arch portion; and,
   e. at least one stanchion comprised in said base and extending beneath the at least one projection along said perpendicular direction, said support structure including said pin being movable between (i) an idle position in which said support structure and said pin are supported above the liquid by said shoulder portion, in contact with said arch, and said pin is positioned above the test piece, and (ii) a test position in which said at least one projection rests upon said at least one stanchion, said test piece is immersed within said liquid, said shoulder is separated from said arch, and an extremity of said pin presses said test piece between said ends thereof.

2. A device according to claim 1, wherein the arch portion comprises a bore in which the pin is slidably mounted.

3. A device according to claim 1, and further comprising means for measuring deflection of the test piece during testing thereof.

4. A device according to claim 3, wherein the means for measuring the deflection of the test piece comprises a rod which traverses the pin and extends as far as the test piece and at least one reference scale secured to the base.

5. A device according to claim 4, wherein the extremity of the pin comprises a lever linked to the pin by joint means and provided with two pressing knives for impinging on the test piece on both sides of the joint means.

6. A device according to claim 5, wherein the rod traverses the joint means.

7. A device according to claim 1, wherein the support structure also comprises means for immobilizing the test piece on the supports.

8. A device according to claim 1, wherein the at least one stanchion comprises grooves in which the at least one projection is slidably mounted.

9. A device according to claim 1, and further comprising means for centering the pin between the ends of the test piece.

* * * * *